United States Patent
Burg et al.

(10) Patent No.: US 7,846,336 B2
(45) Date of Patent: Dec. 7, 2010

(54) CHROMATOGRAPHIC METHODS

(75) Inventors: Josef Burg, Weilheim (DE); Klaus Reichert, Oberhausen (DE); Axel Schroth, Sindelsdorf (DE); Hartmut Schurig, Loerrach (DE); Axel Wessner, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 287 days.

(21) Appl. No.: 12/218,543

(22) Filed: Jul. 16, 2008

(65) Prior Publication Data

US 2009/0101585 A1 Apr. 23, 2009

(51) Int. Cl.
*B01D 15/08* (2006.01)

(52) U.S. Cl. ........................ 210/656; 210/635; 210/638; 210/198.2; 530/416

(58) Field of Classification Search ................. 210/635, 210/638, 656, 670, 672, 673; 530/416
See application file for complete search history.

(56) References Cited

U.S. PATENT DOCUMENTS

| | | |
|---|---|---|
| 6,583,272 B1 | 6/2003 | Bailon |
| 7,169,754 B2 | 1/2007 | Papadimitriou |
| 2003/0148005 A1 | 8/2003 | Chang et al. |
| 2008/0230478 A1* | 9/2008 | Johansson et al. ............ 210/656 |
| 2009/0101585 A1* | 4/2009 | Burg et al. ................... 210/673 |

FOREIGN PATENT DOCUMENTS

| | | |
|---|---|---|
| EP | 0 536 447 | 10/1997 |
| EP | 1 064 951 | 1/2001 |
| WO | WO-2004/024866 | 3/2004 |
| WO | WO-2006/011839 | 2/2006 |
| WO | WO-2006/125599 | 11/2006 |
| WO | WO-2007/041713 | 4/2007 |

OTHER PUBLICATIONS

Ake Danielsson, et al., "One-step purification of monoclonal IgG antibodies from mouse ascites," Journal of Immunological Methods, 115 (1988) 79-88.

Haibo Wang, et al., "High-level expression of human TFF3 in *Escherichia coli*," Peptides, 26 (2005) 1213-1218.

Pengzhan Yu, et al., "Facile purification of mono-PEGylated interleukin-1 receptor antagonist and its characterization with multi-angle laser light scattering," Process Biochemistry, 42 (2007) 971-977.

Qiang Yun, et al., "Reproducible preparation and effective separation of PEGylated recombinant human granulocyte colony-stimulating factor with novel "PEG-pellet" PEGylation mode and ion-exchange chromatography," Journal of Biotechnology, 118 (2005) 67-74.

* cited by examiner

*Primary Examiner*—Ernest G Therkorn
(74) *Attorney, Agent, or Firm*—Fulbright & Jaworski LLP (57) ABSTRACT

The current invention comprises a method for the regeneration of a cation exchange chromatography column.

4 Claims, 2 Drawing Sheets

SEQUENCE LISTING

<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

```
Gly Ala Gln Lys Glu Ala Ile Ser Pro Pro Asp Ala Ala Ser Ala Ala
        115             120             125

Pro Leu Arg Thr Ile Thr Ala Asp Thr Phe Arg Lys Leu Phe Arg Val
    130             135             140

Tyr Ser Asn Phe Leu Arg Gly Lys Leu Lys Leu Tyr Thr Gly Glu Ala
145             150             155             160

Cys Arg Thr Gly Asp Arg
                165
```

CHROMATOGRAPHIC METHODS

PRIORITY TO RELATED APPLICATION(S)

This application claims the benefit of European Patent Application No. 07013960.5, filed Jul. 17, 2007, which is hereby incorporated by reference in its entirety.

The current invention is in the field of chromatographic separation methods useful for the purification of polypeptides, especially of PEGylated polypeptides.

BACKGROUND OF THE INVENTION

Proteins play an important role in today's medical portfolio. For human application every therapeutic protein has to meet distinct criteria. To ensure the safety of biopharmaceutical agents to humans by-products accumulating during the production process have to be removed especially. To fulfill the regulatory specifications one or more purification steps have to follow the manufacturing process. Among other things, purity, throughput, and yield play an important role in determining an appropriate purification process.

Different methods are well established and widespread used for protein purification, such as affinity chromatography with microbial proteins (e.g., protein A or protein G affinity chromatography), ion exchange chromatography (e.g., cation exchange (sulfopropyl or carboxymethyl resins), anion exchange (amino ethyl resins) and mixed-mode ion exchange), thiophilic adsorption (e.g., with beta-mercaptoethanol and other SH ligands), hydrophobic interaction or aromatic adsorption chromatography (e.g., with phenyl-sepharose, aza-arenophilic resins, or m-aminophenylboronic acid), metal chelate affinity chromatography (e.g., with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

Conjugations are reported, for example, for polyethylene glycol (PEG) and Interleukin-6 (EP 0 442 724), for PEG and erythropoietin (WO 01/02017), for chimeric molecules comprising Endostatin and immunoglobulins (US 2005/008649), for secreted antibody based fusion proteins (US 2002/147311), for fusion polypeptides comprising albumin (US 2005/0100991; human serum albumin U.S. Pat. No. 5,876,969), for PEGylated polypeptides (US 2005/0114037), and for interferon fusions.

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun. Meth. 115 (1988), 79-88. A method for purifying a polypeptide by ion exchange chromatography is reported in WO 2004/024866 in which a gradient wash is used to resolve a polypeptide of interest from one or more contaminants. In EP 0 530 447 a process for purifying IgG monoclonal antibodies by a combination of three chromatographic steps is reported. A facile purification of mono-PEGylated interleukin-1 receptor antagonist is reported by Yu, G., et al., in Process Biotechnol. 42 (2007) 971-977. Wang et al. (Wang, H., et al., Peptides 26 (2005) 1213-1218) reports the purification of hTFF3 expressed in *E.coli* by a two step cation exchange chromatography. Yun et al. (Yun, Q., et al., J. Biotechnol. 118 (2005) 67-74) report the purification of PEGylated rhG-CSF by two consecutive ion-exchange chromatography steps.

SUMMARY OF THE INVENTION

One aspect of the current invention is a method for the regeneration of a cation exchange chromatography column after the elution of compounds of interest comprising the following steps in this order:
eluting adsorbed polypeptides from the column with an aqueous buffered solution comprising sodium chloride at a concentration of at least 500 mM,
flushing the column with purified water,
applying a 0.5 M sodium hydroxide solution to the column,
flushing the column with purified water,
applying a solution comprising 0.5 M sodium dihydrogen phosphate and 1 M phosphoric acid to the column,
flushing the column with purified water,
applying a 0.5 M sodium hydroxide solution to the column for at least 4 hours, and
regenerating the cation exchange column by flushing the column with purified water.

DETAILED DESCRIPTION OF THE INVENTION

The current invention provides in a first aspect, a method for the regeneration of a cation exchange chromatography column after the elution of compounds of interest comprising the following steps:
removing any residual bound polypeptides from the cation exchange column with a aqueous buffered solution comprising sodium chloride, followed by
flushing the cation exchange column with purified water, followed by
applying a sodium hydroxide solution to the cation exchange column, followed by
flushing the column with purified water, followed by
applying a solution comprising sodium dihydrogen phosphate and phosphoric acid to the cation exchange column, followed by
flushing the cation exchange column with purified water, followed by
applying a 0.5 M sodium hydroxide solution to the cation exchange column for at least 4 hours, and
regenerating the cation exchange column by flushing the cation exchange column with purified water.

The term "purified water" as used within this application denotes water for injection according to the US Pharmacopeia.

The term "ion exchange material" as used within this application denotes an immobile, high molecular weight matrix that carries covalently bound charged substituents that are used as stationary phase in ion exchange chromatography. For overall charge neutrality nor covalently bound counter ions are bound thereto. The "ion exchange material" has the ability to exchange its nor covalently bound counter ions for similarly charged ions of the surrounding solution. Depending on the charge of its exchangeable counter ions the "ion exchange resin" is referred to as a cation exchange resin or as an anion exchange resin. Depending on the nature of the charged group (substituent), the "ion exchange resin" is referred to in the case of cation exchange resins, as sulfonic acid resin (S), sulfopropyl resin (SP), or carboxymethyl resin (CM). Depending on the chemical nature of the charged group/substituent the "ion exchange resin" can also be classified as a strong or weak ion exchange resin, depending on the strength of the covalently bound charged substituent. For example, strong cation exchange resins have a sulfonic acid group, preferably a sulfopropyl group, as the charged substituent, while weak cation exchange resins have a carboxylic group, preferably a carboxymethyl group, as the charged substituent, and weak anion exchange resins have a diethylaminoethyl group as the charged substituent. In one embodiment, the cation exchange chromatography column contains a sulfopropyl cation exchange resin, i.e., it is a sulfopropyl cation exchange chromatography column.

Different types of ion exchange materials, i.e., stationary phases, are available under different names and from a multitude of companies such as e.g., cation exchange materials Bio-Rex® (e.g., type 70), Chelex® (e.g., type 100), Macro-Prep® (e.g., type CM, High S, 25 S), AG® (e.g., type 50W, MP) all available from BioRad Laboratories, WCX 2 available from Ciphergen, Dowex® MAC-3 available from Dow chemical company, Mustang C and Mustang S available from Pall Corporation, Cellulose CM (e.g., type 23, 52), hyper-D, partisphere available from Whatman plc., Amberlite® IRC (e.g., type 76, 747, 748), Amberlite® GT 73, Toyopearl® (e.g., type SP, CM, 650M) all available from Tosoh Bioscience GmbH, CM 1500 and CM 3000 available from Bio-Chrom Labs, SP-Sepharose™, CM-Sepharose™ available from GE Healthcare, Poros resins available from PerSeptive Biosystems, Asahipak ES (e.g., type 502C), CXpak P, IEC CM (e.g., type 825, 2825, 5025, LG), IEC SP (e.g., type 420N, 825), IEC QA (e.g., type LG, 825) available from Shoko America Inc., 50W cation exchange resin available from Eichrom Technologies Inc. In one embodiment the cation exchange material is a strong cation exchange material such as Macro-Prep® High S or 25S, or MacroCap SP, or Toyopearl®D SP 650M, or Source S, or SP Sepharose, or POLYCAT A. Exemplary anion exchange materials are Dowex® 1 available from Dow chemical company, AG® (e.g., type 1, 2, 4), Bio-Rex® 5, DEAE Bio-Gel 1, Macro-Prep® DEAE all available from BioRad Laboratories, anion exchange resin type 1 available from Eichrom Technologies Inc., Source Q, ANX Sepharose 4, DEAE Sepharose (e.g., type CL-6B, FF), Q Sepharose, Capto Q, Capto S all available from GE Healthcare, AX-300 available from PerkinElmer, Asahipak ES-502C, AXpak WA (e.g., type 624, G), IEC DEAE all available from Shoko America Inc., Amberlite® IRA-96, Toyopearl® DEAE, TSKgel DEAE all available from Tosoh Bioscience GmbH, Mustang Q available from Pall Corporation.

The term "flushing" as used within this application denotes the washing of a column with two or more column volumes of a specified solution.

The term "same type of cation exchange material" denotes two consecutive ion exchange chromatography steps which are performed by employing an identical cation exchange material. This means that the consecutive cation exchange chromatography steps are carried out by using either a first portion of the cation exchange material for the first cation exchange chromatography step and by using the second portion of the same cation exchange material for the second cation exchange chromatography or by using the same cation exchange material for both cation exchange chromatography steps.

The terms "step elution" and "step elution method", which are used interchangeably within this application, denote a method wherein the concentration of a substance causing elution, i.e., the dissolution of a bound compound from a material, is raised or lowered at once, i.e., directly from one value/level to the next value/level. In this "step elution" one or more conditions, for example the pH, the ionic strength, concentration of a salt, and/or the flow of a chromatography, is/are changed all at once from a first, e.g., starting, value to a second, e.g., final, value, i.e., the conditions are changed incrementally, i.e., stepwise, in contrast to a linear change. In the "step elution method" a new fraction is collected after each increase in the ionic strength. This fraction contains the compounds recovered from the ion exchange material with a corresponding increase in ionic strength. After each increase the conditions are maintained until the next step in the elution method is carried out.

The terms "continuous elution" and "continuous elution method", which are used interchangeably within this application, denote a method wherein the concentration of a substance causing elution, i.e., the dissolution of a bound compound from a material, is raised or lowered continuously, i.e., the concentration is changed by a sequence of small steps each of which is not larger than a change of 2%, preferably of 1%, of the concentration of the substance causing elution. In this "continuous elution" one or more conditions, for example the pH, the ionic strength, concentration of a salt, and/or the flow of a chromatography, may be changed linearly or exponentially or asymptotically. Preferably the change is linear.

The term "applying to" and grammatical equivalents thereof as used within this application denotes a partial step of a purification method in which a solution containing, e.g., a substance of interest to be purified, is brought in contact with a stationary phase. This denotes that a) the solution is added to a chromatographic device in which the stationary phase is located, or b) that a stationary phase is added to the solution. In case a) the solution containing, e.g., the substance of interest to be purified, passes through the stationary phase, allowing for an interaction between the stationary phase and the substances in solution. Depending on the conditions, such as pH, conductivity, salt concentration, temperature, and/or flow rate, some substances in the solution are bound to the stationary phase and, thus, are removed from the solution. Other substances remain in solution or are desorbed from the stationary phase. The substances in solution can be found in the flow-through. The "flow-through" denotes the solution obtained after the passage through the chromatographic device, which may either be the applied solution containing the substance of interest or the buffer, which is used to flush the column or to cause elution of one or more substances bound to the stationary phase. In one embodiment the chromatographic device is a column, or a cassette. The substance of interest can be recovered from the solution after the purification step by methods familiar to a person of skill in the art, such as precipitation, salting out, ultrafiltration, diafiltration, lyophilization, affinity chromatography, or solvent volume reduction, to obtain the substance of interest in substantially homogeneous form. In case b) the stationary phase is added, e.g., as a solid, to the solution containing, e.g., the substance of interest to be purified, allowing for an interaction between the stationary phase and the substances in solution. After the interaction the stationary phase is removed, e.g., by filtration, whereby the substance of interest is either bound to the stationary phase and removed therewith from the solution or remains unbound to the stationary phase and remains in the solution.

The term "under conditions suitable for binding" and grammatical equivalents thereof as used within this application denotes that a substance of interest, e.g., PEGylated erythropoietin, binds to a stationary phase, e.g., an ion exchange material when brought in contact with it. This does not necessarily mean that 100% of the substance of interest is bound but that essentially 100% of the substance of interest is bound, i.e., at least 50% of the substance of interest is bound, preferably at least 75% of the substance of interest, more preferably at least 85% of the substance of interest, and even more preferably more than 95% of the substance of interest is bound to the stationary phase.

The term "buffered" as used within this application refers to a solution in which changes of pH due to the addition or release of acidic or basic substances is leveled by a buffer substance. Any buffer substance resulting in such an effect can be used. In one embodiment, pharmaceutically acceptable buffer substances are used, such as phosphoric acid or salts thereof, acetic acid or salts thereof, citric acid or salts thereof, morpholine, 2-(N-morpholino) ethanesulfonic acid or salts thereof, histidine or salts thereof, glycine or salts thereof, or tris (hydroxymethyl) aminomethane (TRIS) or salts thereof. In preferred embodiments, phosphoric acid or salts thereof, acetic acid or salts thereof, citric acid or salts thereof, histidine or salts thereof are used. Optionally, the buffered solution may comprise one or more additional salts, such as sodium chloride, sodium sulphate, potassium chloride, potassium sulfate, sodium citrate, or potassium citrate.

General chromatographic methods and their use are known to a person skilled in the art. See for example, Chromatography, $5^{th}$ edition, Part A: Fundamentals and Techniques, Heftmann (ed) Elsevier Science Publishing Company 1992 Chromatography $5^{th}$ ed 51 A 1992; Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

The PEGylation of erythropoietin normally results in a mixture of different compounds, such as poly-PEGylated erythropoietin, mono-PEGylated erythropoietin, not-PEGylated erythropoietin, hydrolysis products of the activated PEG ester, as well as hydrolysis products of the erythropoietin itself. In order to obtain a mono-PEGylated erythropoietin in substantially homogeneous form these substances have to be separated and the compound of interest has to be purified.

Therefore, it is the second aspect of the current invention to provide a method for obtaining a mono-PEGylated erythropoietin in substantially homogenous form comprising the following steps:
a) PEGylating erythropoietin using an activated PEGylating reagent of a molecular weight of from 20 kDa to 40 kDa,
b) purifying the PEGylated erythropoietin obtained in step a) with two consecutive cation exchange chromatography steps, wherein the first and second cation exchange chromatography steps employ the same type of cation exchange material,
c) recovering the mono-PEGylated erythropoietin from the second cation exchange chromatography column in a substantially homogeneous form,
d) regenerating the cation exchange chromatography column by a method according to the invention.

This method is especially useful for the purification of PEGylated recombinant polypeptides, which are glycosylated, i.e., which have been produced by a mammalian cell, preferably a CHO cell, HEK293 cell, BHK cell, Per.C6® cell, or HeLa cell and are afterwards chemically PEGylated. In one embodiment the regeneration of a cation exchange chromatography column comprises the following steps:

removing bound polypeptides from the cation exchange column with an aqueous buffered solution comprising sodium chloride,
flushing the column with purified water, preferably with at least two column volumes,
applying a sodium hydroxide solution to the column, preferably at least two column volumes,
flushing the column with purified water, preferably with at least two column volumes,
applying a solution comprising sodium dihydrogen phosphate and phosphoric acid to the column, preferably at least three column volumes,
flushing the column with purified water, preferably with at least two column volumes,
applying a 0.5 M sodium hydroxide solution to the column for at least 4 hours, preferably for 4 hours, and
regenerating the cation exchange column by flushing the column with purified water, preferably with at least two column volumes.

In the first step of the method, erythropoietin is PEGylated. The poly (ethylene glycol) (PEG) polymer molecules used in the PEGylation reaction have a molecular weight of about 20 kDa to 40 kDa (by "molecular weight" as used here there is to be understood the mean molecular weight of the PEG because PEG as a polymeric compound is not obtained with a defined molecular weight but in fact has a molecular weight distribution; the term "about" indicates that in said PEG preparations, some molecules will weigh more and some less than the indicated molecular weight, i.e the term "about" refers to a molecular weight distribution in which 95% of the PEG molecules have a molecular weight within +/−10% of the indicated molecular weight. For example, a molecular weight of 30 kDa denotes a range of from 27 kDa to 33 kDa).

The term "erythropoietin" refers to a protein having the amino acid sequence of SEQ ID NO: 1 or SEQ ID NO: 2, or a protein or polypeptide substantially homologous thereto, whose biological properties relate to the stimulation of red blood cell production and the stimulation of the division and differentiation of committed erythroid progenitors in the bone marrow. Recombinant erythropoietin may be prepared via expression in eukaryotic cells, for example in CHO cells, or BHK cells, or HeLa cells by recombinant DNA technology or by endogenous gene activation, i.e., the erythropoietin glycoprotein is expressed by endogenous gene activation. See, for example U.S. Pat. No. 5,733,761, U.S. Pat. No. 5,641,670, U.S. Pat. No. 5,733,746, WO 93/09222, WO 94/12650, WO 95/31560, WO 90/11354, WO 91/06667, and WO 91/09955. In one embodiment the erythropoietin according to the invention is based on the sequence of human EPO. In a preferred embodiment the human erythropoietin has the amino acid sequence set out in SEQ ID NO: 1 or SEQ ID NO: 2, more preferably the human erythropoietin has the amino acid sequence set out in SEQ ID NO: 1. The term "erythropoietin" also denotes variants of the protein of SEQ ID NO: 1 or SEQ ID NO: 2, in which one or more amino acid residues have been changed, deleted, or inserted, and which has the same biological activity as the non-modified protein, such as e.g., reported in EP 1 064 951, or U.S. Pat. No. 6,583,272. A variant may have the amino acid sequence of human erythropoietin having from 1 to 6 additional sites for glycosylation. The specific activity of PEGylated erythropoietin can be determined by various assays known in the art. The biological activity of the purified PEGylated erythropoietin of this invention are such that administration of the protein by injection to human patients results in bone marrow cells increasing production of reticulocytes and red blood cells compared to non-injected or control groups of subjects. The biological activity of the PEGylated erythropoietin obtained and purified in accordance with this invention can be tested by methods according to Pharmeuropa Spec. Issue Biologicals BRP Erythropoietin Bio 97-2 (1997) 31-48.

"PEG" or "PEG group" according to the invention means a residue containing poly (ethylene glycol) as an essential part. Such a PEG can contain further chemical groups, which are necessary for binding reactions, which results from the chemical synthesis of the molecule, or which are spacers for optimal distance of parts of the molecule. These further chemical groups are not used for the calculation of the molecular weight of the PEG polymer molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. Branched PEG are described in, for example, EP 0 473 084, U.S. Pat. No. 5,932,462. Linear PEG molecules with a molecular weight of 20-35 kDa molecules are used in one embodiment and branched PEG polymers with a molecular weight of more than 35 kDa, especially with 40 kDa, are used in another embodiment. A 40 kDa, a two-armed PEG is particularly preferred.

The term "PEGylation" means a covalent linkage of a poly (ethylene glycol) residue at the N-terminus of the polypeptide and/or an internal lysine residue. PEGylation of proteins is widely known in the state of the art and is reviewed by, for example, Veronese, F. M., Biomaterials 22 (2001) 405-417. PEG can be linked using different functional groups and poly (ethylene glycol)s with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier Systems 9 (1992) 249-304) can be used. PEGylation of erythropoietin can be performed in aqueous solution with PEGylation reagents as described, for example, in WO 00/44785, in one embodiment, using NHS-activated linear or branched PEG molecules with a molecular weight between 5 kDa and 40 kDa. PEGylation can also be performed at the solid phase according to Lu, Y., et al., Reactive Polymers 22 (1994) 221-229. Not randomly, N-terminally PEGylated polypeptide can also be produced according to WO 94/01451.

Such methods result in an erythropoietin which is PEGylated at one or more ε-amino groups of lysine residues and/or at the N-terminal amino group. Selective PEGylation at the N-terminal amino acid can be performed according to Felix, A. M., et al., ACS Symp. Ser. 680 (Poly(ethylene glycol)) (1997) 218-238. Selective N-terminal PEGylation can be achieved during solid-phase synthesis by coupling of a $N^\alpha$-PEGylated amino acid derivative to the N−1 terminal amino acid of the peptide chain. Side chain PEGylation can be performed during solid-phase synthesis by coupling of $N^\epsilon$-PEGylated lysine derivatives to the growing chain. Combined N-terminal and side chain PEGylation is feasible either as described above within solid-phase synthesis or by solution phase synthesis by applying activated PEG reagents to an amino deprotected peptide.

Suitable PEG derivatives are activated PEG molecules with in one embodiment an average molecular weight of from about 5 to about 40 kDa, in a preferred embodiment of from about 20 to about 40 kDa, and in a more preferred embodiment of about 30 kDa to about 35 kDa. The PEG derivatives can be linear or branched PEGs. A wide variety of PEG derivatives suitable for use in the preparation of PEG-protein and PEG-peptide conjugates can be obtained from Shearwater Polymers (Huntsville, Ala., U.S.A.).

Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone (m is in one embodiment an integer of from about 450 to about 900 and R is lower alkyl, linear or branched, having one to six carbon atoms such as methyl, ethyl, isopropyl, etc. whereby methyl is preferred).

The use of these iodo-activated substances is known in the art and described e.g., by Hermanson, G. T., in Bioconjugate Techniques, Academic Press, San Diego (1996) p. 147-148.

In one embodiment the PEG species is an activated PEG ester, e.g., N-hydroxysuccinimidyl propionate, or N-hydroxysuccinimidyl butanoate, or N-hydroxysuccinimides such as PEG-NHS (Monfardini, C., et al., Bioconjugate Chem. 6 (1995) 62-69). In one embodiment the PEG is activated by N-hydroxysuccinimide ester using alkoxy-PEG-N-hydroxysuccinimide, such as methoxy-PEG-N-hydroxysuccinimide (MW 30000; Shearwater Polymers, Inc.), wherein R and m are as defined above. In one embodiment the PEG species is the N-hydroxysuccinimidyl ester of methoxy poly (ethylene glycol)-butyric acid. The term "alkoxy" refers to an alkyl ether group in which the term 'alkyl' means a straight-chain or branched-chain alkyl group containing a maximum of four carbon atoms, such as methoxy, ethoxy, n-propoxy and the like, preferably methoxy.

The term "substantially homogeneous form" as used within this application denotes that the PEGylated erythropoietin obtained, contained, or used are those having a defined number of PEG group attached. In one embodiment the PEGylated erythropoietin is a mono-PEGylated erythropoietin. The preparation may contain unreacted (i.e., PEG group lacking) erythropoietin, poly-PEGylated erythropoietin, as well as fragments of the polypeptide generated during the PEGylation reaction. The term "substantially homogeneous form" denotes that a preparation of a mono-PEGylated erythropoietin contains at least 50% (w/w) of the mono-PEGylated erythropoietin, at least 75% of the mono-PEGylated erythropoietin, at least 90% of the mono-PEGylated erythropoietin, or more than 95% of the mono-PEGylated erythropoietin. The percent values are based on the area-% of the chromatogram corresponding to the cation exchange chromatography from which the mono-PEGylated erythropoietin is obtained.

The present invention describes a method for the purification of a mono-PEGylated erythropoietin in order to obtain a substantially homogeneous form of a mono-PEGylated erythropoietin. It has surprisingly been found that the combination of two consecutive cation exchange chromatography steps both of which employ the same type of cation exchange material provides a substantially homogeneous form of a mono-PEGylated erythropoietin. Therefore the current invention provides a method for the purification of a mono-PEGylated erythropoietin comprising the steps of providing a solution comprising mono-, poly-, and not-PEGylated erythropoietin, performing two consecutive cation exchange chromatography steps, recovering the purified mono-PEGylated erythropoietin in the second cation exchange chromatography step, wherein the same type of cation exchange material is used in both cation exchange chromatography steps, and regenerating the cation exchange chromatography column by a method according to the first aspect of the current invention.

The recovery of the purified mono-PEGylated erythropoietin in the second cation exchange chromatography step is carried out by eluting the mono-PEGylated erythropoietin from the second cation exchange chromatography material. In one embodiment of the invention, the two cation exchange chromatography steps differ in the elution method employed. The first cation exchange chromatography step is performed in one embodiment, as a step elution method, i.e., the ionic strength of the used buffer is increased stepwise, i.e., at once, from one ionic strength value to the next ionic strength value. The step elution method is performed in one embodiment as a three step elution method. In the first step mainly poly-PEGylated erythropoietin is eluted from the cation exchange chromatography column. The second increase in ionic strength basically elutes the mono-PEGylated erythropoietin with a purity of more than 60% based on the area of the corresponding size-exclusion chromatogram (area-%). The third increase in ionic strength elutes mainly the remaining not-PEGylated erythropoietin from the column.

The second cation exchange chromatography step is performed in one embodiment as a continuous elution method, i.e., the ionic strength of the buffer is increased continuously. The eluted fractions containing the mono-PEGylated erythropoietin are combined in order to obtain a mono-PEGylated erythropoietin in substantially homogeneous form, containing in one embodiment less than 0.5% of low molecular weight forms based on the area of the corresponding chromatogram. The buffer is in one embodiment present in a concentration of from 10 mM to 250 mM, preferably of from 50 mM to 150 mM, more preferably at about 100 mM.

Therefore, in the method according to the invention the two consecutive cation exchange chromatography steps are the following:

a) applying an aqueous, buffered solution comprising a mixture of mono-, poly-, and non-PEGylated erythropoietin to a first cation exchange chromatography column under conditions suitable for binding of said mono-PEGylated erythropoietin to the cation exchange material contained in said first column, b) recovering a mono-PEGylated erythropoietin from the first cation exchange chromatography column by a step elution method with a stepwise increase of the ionic strength of the through flowing buffer, wherein the relative content of mono-PEGylated erythropoietin is increased compared to the applied mixture of step a), c) applying the recovered mono-PEGylated erythropoietin from step b) to a second cation exchange chromatography column under conditions suitable for binding of said erythropoietin to the cation exchange material contained in said second column, whereby the cation exchange material contained in said second column is of the same type as the cation exchange material in the first column, d) recovering the purified mono-PEGylated erythropoietin in a substantially homogeneous form from said second cation exchange chromatography column by a continuous elution method with a continuous increase of the ionic strength of the through flowing buffer.

The PEGylation of a polypeptide does normally not provide the PEGylation product in homogeneous form. Rather, it is obtained as a mixture of mono-PEGylated, poly-PEGylated, and non-PEGylated product. Therefore the solution of the PEGylated erythropoietin applied in step a) of the method is a mixture of mono-, poly-, and non-PEGylated erythropoietin and low molecular weight forms or fragments in an aqueous buffer. The relative content of the different substances is determined by size exclusion chromatography (SE-HPLC). The sum of the area of the correlated peaks, i.e., the area under the peaks, in the size exclusion chromatogram is the total area of the size-exclusion chromatogram. The fraction of a single peak is given as area-%, i.e., as relative area fraction of the total area of the chromatogram.

General chromatographic methods, their use, and the related terms are known to a person skilled in the art. See for example, Chromatography, $5^{th}$ edition, Part A: Fundamentals and Techniques, Heftmann (ed.), Elsevier Science Publishing Company, Chromatography $5^{th}$ ed., 51 A (1992) and other related textbooks. During the chromatography a buffer is flowing through the cation exchange chromatography column. This "through flowing buffer" is adjusted according to the requirements of the steps of the chromatography method. It transports the substance of interest to (applying) and from (eluting) the chromatographic material.

In the first cation exchange chromatography step the mixture of mono-PEGylated, poly-PEGylated, and not-PEGylated erythropoietin is applied at a protein concentration of about 1 mg/ml to the first cation exchange chromatography column in an aqueous solution buffered with about 100 mM potassium phosphate at about pH 3.0. The term "about" as used within the current application denotes a range of 10% around the given value, i.e., ±10%. Prior to and after the application the first column is washed with the same buffer solution. For the first step in the step elution method the buffer is changed to a buffer with about 100 mM potassium phosphate, about 90 mM sodium chloride at about pH 3.0. In using this buffer hydrolyzed PEG reagent, i.e., the corresponding PEGylated carbonic acid, unreacted coupling reagent, and poly-PEGylated erythropoietin are eluted from the cation exchange chromatography column. For the second step in the three step elution method the buffer is changed to a buffer with about 100 mM potassium phosphate, about 250 mM sodium chloride at about pH 3.0. In this step the mono-PEGylated erythropoietin is recovered from the first cation exchange chromatography column. The collected through flowing buffer of this elution step is diluted approximately 1:5 to 1:8 with purified water. After the first cation exchange chromatography step the recovered mono-PEGylated erythropoietin is free of free PEG.

The collected, through flowing buffer of the second step of the first cation exchange chromatography contains the mono-PEGylated erythropoietin in an increased relative content, i.e the fraction by weight or by area-% (in the chromatogram of a size exclusion chromatography of the collected through flowing buffer of the second step) of the mono-PEGylated erythropoietin has increased when compared to prior to the first cation exchange chromatography step. In one embodiment, the relative content of mono-PEGylated erythropoietin is at least 60 area-%. In a preferred embodiment, the relative content of mono-PEGylated erythropoietin is at least 80 area-%.

For further purification of the mono-PEGylated erythropoietin a second cation exchange chromatography step is performed. For the second cation exchange chromatography the collected and diluted through flowing buffer of the second elution step is adjusted to a potassium phosphate concentration of about 100 mM and to a pH of about pH 3.0 and is applied to a second cation exchange chromatography column containing a cation exchange material of the same type as the first cation exchange chromatography column. In one embodiment, the second cation exchange column and the cation exchange material contained therein are the same as in the first cation exchange chromatography step. The mono-PEGylated erythropoietin is recovered from the second cation exchange chromatography column by applying a linear gradient starting with potassium phosphate buffer at a concentration of about 100 mM with about 50 mM sodium chloride at about pH 3.0 and ending with a potassium phosphate buffer of a concentration of about 100 mM with about 500 mM sodium chloride at about pH 3.0. The change in the sodium chloride concentration is linear over ten column volumes. The through flowing buffer is fractioned and each fraction is diluted with 1 M dipotassium hydrogen phosphate to increase the pH value to about pH 6 to 8.

After the second cation exchange chromatography step the mono-PEGylated erythropoietin is obtained in substantially homogeneous form, preferably with a purity of at least 95% by area.

A person of skill in the art is familiar with the technology of ion exchange chromatography. In the step leading to recovery of the polypeptide bound to the cation exchange material the ionic strength, i.e., the conductivity, of the buffer/solution passing through the ion exchange column is increased. This can be accomplished either by an increased buffer salt concentration or by the addition of other salts, so called elution salts, to the buffer solution. Depending on the elution method the buffer/salt concentration is increased at once (step elution method) or continuously (continuous elution method) by the fractional addition of a concentrated buffer or elution salt solution. In one embodiment the elution salt is sodium citrate, sodium chloride, sodium sulphate, sodium phosphate, potassium chloride, potassium sulfate, potassium phosphate, or other salts of citric acid or phosphoric acid, or any mixture of these components. In a preferred embodiment the elution salt is sodium citrate, sodium chloride, potassium chloride, or mixtures thereof.

In one embodiment of the invention, the cation exchange material is a strong cation exchange material. In a preferred embodiment, there is Toyopearl® SP 650 M. In another preferred embodiment, it is a sulfopropyl cation exchange material. The concentration of the salt, causing the elution, is in one embodiment in the range of from 5 mM to 500 mM. In a preferred embodiment, the concentrated range from 5 mM to 400 mM, and in an especially preferred embodiment, from 5 mM to 250 mM. In another embodiment of the invention, the salt causing the elution for example citric acid or salts thereof or phosphoric acid or salts thereof is also used as buffer substance The mono-PEGylated erythropoietin may be used in pharmaceutical compositions suitable for injection with a pharmaceutically acceptable carrier or vehicle by methods known in the art. For example, appropriate compositions have been described in WO 97/09996, WO 97/40850, WO 98/58660, and WO 99/07401. Among the preferred, pharmaceutically acceptable carriers for formulating the products of the invention are human serum albumin, human plasma proteins, etc. The compounds of the present invention may be formulated in 10 mM sodium/potassium phosphate buffer at pH 7 containing a tonicity agent, e.g., 132 mM sodium chloride. Optionally the pharmaceutical composition may contain a preservative. The pharmaceutical composition may contain different amounts of mono-PEGylated erythropoietin, e.g., 10-1000 µg/ml, e.g., 50 µg or 400 µg.

Administration of the erythropoietin glycoprotein products of the present invention results in red blood cell formation in humans. Therefore, administration of the mono-PEGylated erythropoietin glycoprotein product replenishes this erythropoietin protein which is important in the production of red blood cells. The pharmaceutical compositions containing the mono-PEGylated erythropoietin glycoprotein products may be formulated at a strength effective for administration by various means to a human patient experiencing blood disorders characterized by low or defective red blood cell production, either alone or as part of a condition or disease. The pharmaceutical compositions may be administered by injection such as by subcutaneous or intravenous injection. Average quantities of the mono-PEGylated erythropoietin glycoprotein product may vary. The exact amount of conjugate is a matter of preference subject to factors such as the exact type of condition being treated, the condition of the patient being treated, as well as the other ingredients in the composition. For example, 0.01 to 10 µg per kg body weight, preferably 0.1 to 1 µg per kg body weight, may be administered e.g. once weekly.

It has surprisingly been found that a cation exchange chromatography column can be regenerated with a method according to the invention without a considerable decline in the separation efficiency. It has been shown that, using a regeneration method according to the invention, a cation exchange chromatography column can be used for at least 40 separation cycles, in one embodiment for at least 50 separation cycles, in a further embodiment for at least 60 separation cycles without a considerable decline in the separation efficiency (see FIG. 1) and yield (see FIG. 2). The term "separation cycle" as used within this application denotes the sequence i) equilibration of the column, ii) application of the solution to be separated on the column, iii) washing the column, iv) recovering the adsorbed compounds from the column, v) washing the column, vi) regenerating the column. It has also been found that with the regeneration method according to the invention not only can a decline in the separation efficiency be avoided but a decline in the loading capacity can also be prevented (see FIG. 2).

The term "separation efficiency" as used within this application denotes the ability of a cation exchange chromatography column to separate the compounds of a solution. The term "without a considerable decline" as used within this application denotes that the cation exchange chromatography column provides the same, i.e., within in variation of +/−5%, in one embodiment within a variation of +/−2.5%, compound separation in consecutive chromatographies of a solution containing the same compounds. The term "loading capacity" as used within this application denotes the amount of a compound of interest that is recovered from a cation exchange chromatography column.

The following examples, sequence listing and figures are provided to aid the understanding of the present invention, the true scope of which is set forth in the appended claims. It is understood that modifications can be made in the procedures set forth without departing from the spirit of the invention.

Materials And Methods

Se-HPLC

SE-HPLC separates proteins according to their apparent molecular weight. Therefore, the method is able to detect the presence of mono-PEGylated erythropoietin, low molecular weight forms and fragments, poly-PEGylated forms and higher aggregates of erythropoietin. The HPLC is equipped with a 220-nm detector and a Superose 6 HR column (dimensions 10×300 mm, Pharmacia Biotech, Cat-Nr: 17-0537-01) or a Superose 6 10/300 GL column (Pharmacia Biotech, Cat-Nr: 17-5172-01). The column is operated under isocratic conditions at room temperature, using a flow rate of about 0.4 ml/min. The mobile phase buffer is a 50 mM sodium phosphate buffer with 300 mM sodium chloride at pH 6.8. Dependent on the HPLC-system used, the method can be performed with a sample application volume of either 100 μL or 500 μL. The samples are diluted with the mobile phase buffer to a protein concentration of about 0.5 mg/mL (100 μL load) or 0.1 mg/mL (560 μL load). Samples with a protein concentration of less than 0.1 mg/mL can be used undiluted. The eluted proteins are detected at a detector wavelength of 220 nm.

RP-HPLC

Purity is analyzed by RP-HPLC, which separates mono-PEGylated erythropoietin from oligo forms and related substances. The assay is performed on a Poroshell column using an acetonitrile/aqueous TFA gradient. The elution profile is monitored as UV absorbance at 220 nm. The percentage of mono-PEGylated erythropoietin and related substances or oligo forms are calculated based upon the total peak area of the eluted proteins

EXAMPLE 1

Purification of Mono-PEGylated Erythropoietin

Erythropoietin can be produced e.g. according to WO 01/87329, and purified as reported in WO 96/135718. PEGylated erythropoietin can be produced e.g. according to WO 03/029291.

a) First Chromatography on SP Toyopearl 650 M

The first chromatography step was performed on a sulfopropyl (SP) column packed with SP Toyopearl® 650M. The column was operated at room temperature. The maximum loading capacity of the first column was defined as 1.5 g protein per liter column volume (CV). The column was equilibrated with a 100 mM potassium phosphate buffer at a pH of from 2.9 to 3.1 (SP-A buffer). After the loading step, the column was washed and eluted with a series of potassium phosphate buffers containing increasing amounts of NaCl. Free PEGylated carbonic acid, i.e., hydrolyzed PEG reagent, and poly-PEGylated forms were removed in the flow-through and the subsequent washing step with SP-A buffer and 100 mM potassium phosphate buffer, pH 2.9 to 3.1, containing 90 mM sodium chloride (SP-B buffer), respectively. The mono-PEGylated erythropoietin was eluted by applying a 100 mM potassium phosphate buffer, pH 2.9 to 3.1, containing 250 mM sodium chloride (SP-C buffer), collected in a vessel and directly diluted 1:5 with purified water. This collected eluate is termed "SP eluate pool I". The column was subsequently washed with 100 mM potassium phosphate buffer, pH 2.9 to 3.1, containing 750 mM sodium chloride (SP-D buffer) to remove unreacted erythropoietin and the column was regenerated.

b) Second Chromatography on SP Toyopearl 650 M

The second column was operated at room temperature. After equilibration with SP-A buffer the SP eluate pool I was applied to the column and the column was thereafter washed with SP-A buffer. The mono-PEGylated erythropoietin was eluted by applying a linear gradient with a slope of from 50 to 500 mM sodium chloride over ten column volumes, buffered with 100 mM potassium phosphate buffer at pH 2.9 to 3.1. The product peak was fractionated in up to 8 single fractions and each fraction was directly diluted with 1 M dipotassium hydrogen phosphate to increase the pH to 6 to 8. After the elution of mono-PEGylated erythropoietin was completed, the slope of the gradient can be increased leading to an immediate column wash with 100 mM potassium phosphate pH 2.9 to 3.1 containing 500 mM sodium chloride.

c) Regeneration of the SP Toyopearl 650 M Columns

The resins of both columns were regenerated in a sequence of seven steps. The columns were flushed with purified water followed by a 0.5 M sodium hydroxide solution. The alkaline solution was displaced with purified water followed by an acid wash (0.5 M sodium dihydrogen phosphate, 1 M phosphoric acid). After another purified water step, the columns were depyrogenated with 0.5 M sodium hydroxide for $\geq 4$ hours. After caustic regeneration, the columns were washed with purified water again. The purified water (PW III) was produced by ultrafiltration. The quality of PW III is equivalent to that of water for injection according to the US Pharmacopeia. Testing is performed according to the Pharmocopeia referred to previously. During control runs performed according to the above outlined first chromatography step no residual protein or PEG moieties could be detected in the respective through flowing buffers. SDS-PAGE analysis of the resin, after 60 cycles, showed no residual protein or PEG moiety on the gel. Based on these data a batch-to-batch carryover of residual proteins and PEG moiety can be excluded and thus the regeneration of the column is very effective (see also FIG. 1). The determination of the yield obtained in each chromatography showed no decline (see also FIG. 2).

TABLE 1

Summary of parameters for the column regeneration.
Column Parameters

| Step | Buffer Solution | Column Volumes | Flow Rate [L/min] |
| --- | --- | --- | --- |
| Rinse | PW III | $\geq 2$ | 1.6-2.1 |
| Caustic column regeneration I | 0.5 mol/L NaOH | $\geq 2$ | 1.6-2.1 |
| Rinse | PW III | $\geq 2$ | 1.6-2.1 |
| Acid column regeneration | 1 mol/L phosphoric acid 0.5 mol/L sodium dihydrogen phosphate | $\geq 3$ | 1.6-2.1 |
| Rinse | PW III | $\geq 2$ | 1.6-2.1 |
| Caustic column regeneration II | 0.5 mol/L NaOH | $\geq 3$ | n.a. |
| Rinse | PW III | $\geq 2$ | 1.6-2.1 |

Figure 1:
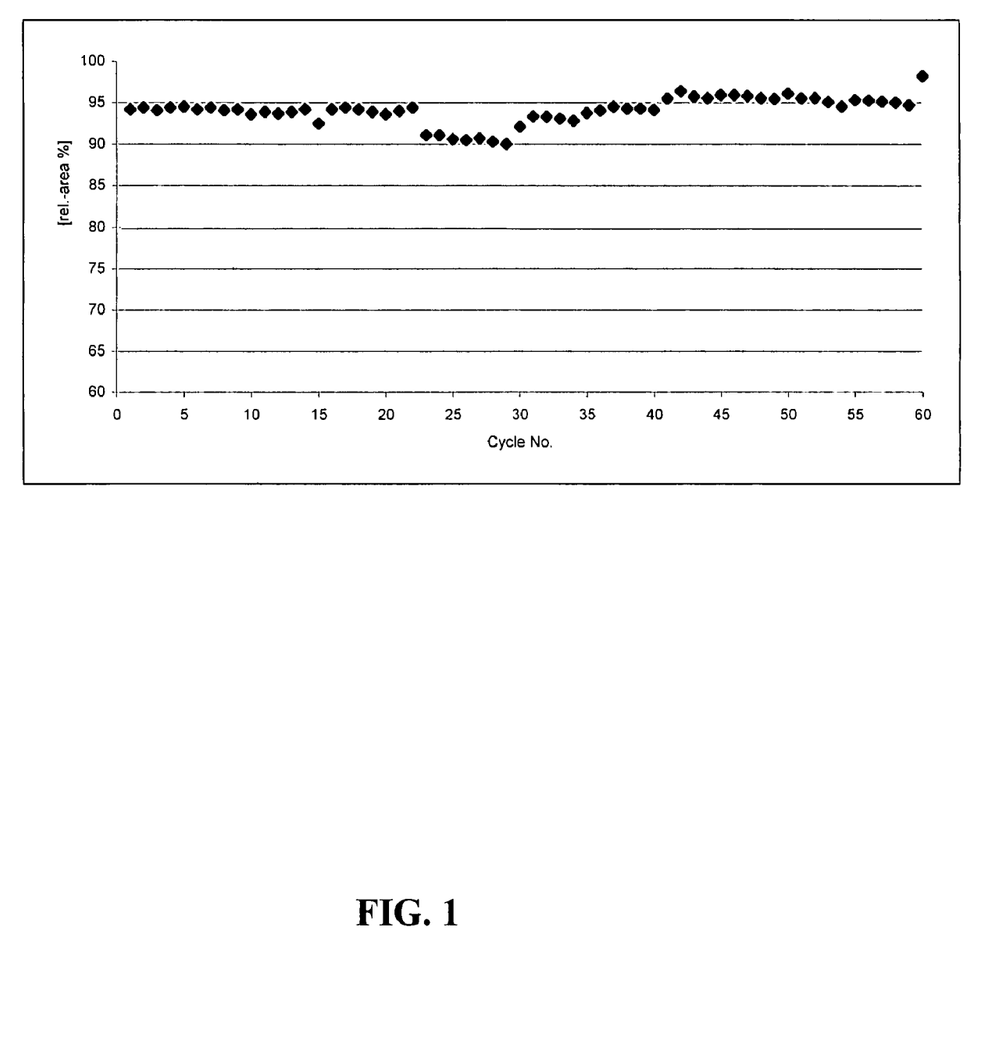
FIG. 1 Purity of mono-PEGylated erythropoietin in the through flowing buffer pool of the first chromatography during cycle number validation of the regeneration process.
Figure 2:
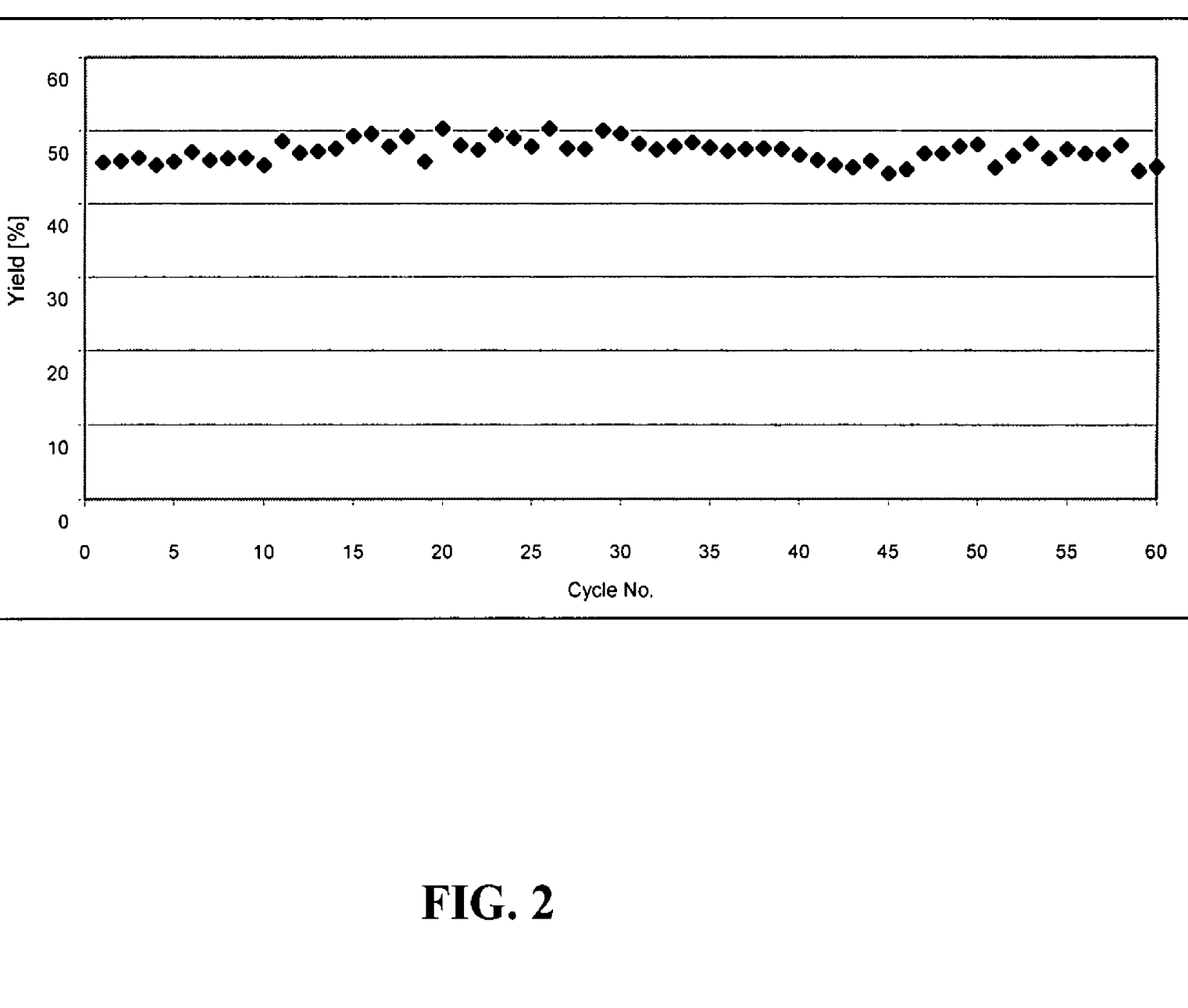
FIG. 2 Yield of mono-PEGylated erythropoietin in the through flowing buffer pool of the first chromatography during cycle number validation of the regeneration process.

As shown in FIGS. 1 and 2, the purity and yield of mono-PEGylated erythropoietin in the through flowing buffer pool for the first chromatography step for all cycles is clearly within the range of at least 80% purity and at least 35% yield. In addition, no trend in purity of mono-PEGylated erythropoietin during the lifetime of the column can be observed.

---

The invention claimed is:

1. A method for regeneration of a cation exchange chromatography column after the elution of a compound of interest comprising:

eluting any adsorbed polypeptides from the column with an aqueous buffered solution comprising sodium chloride at a concentration of at least 500 mM, followed by flushing the column with purified water, followed by applying a 0.5 M sodium hydroxide solution to the column, followed by flushing the column with purified water, followed by applying a solution comprising 0.5 M sodium dihydrogen phosphate and 1 M phosphoric acid to the column, followed by flushing the column with purified water, followed by applying a 0.5 M sodium hydroxide solution to the column for at least 4 hours, and followed by regenerating the cation exchange chromatography column by flushing the column with purified water.

2. The method according to claim 1, wherein said cation exchange chromatography column is a strong cation exchange chromatography column.

3. The method according to claim 2, wherein said cation exchange chromatography column is a sulfopropyl cation exchange chromatography column.

4. The method according to claim 1, wherein said aqueous buffered solution contain phosphoric acid or a salt thereof, acetic acid or a salt thereof, citric acid or a salt thereof, or histidine or a salt thereof.

* * * * *